United States Patent [19]

Kötzsch et al.

[11] 4,417,067
[45] Nov. 22, 1983

[54] METHOD OF CLEAVING ORGANOSILOXANES

[75] Inventors: Hans-Joachim Kötzsch, Rheinfelden; Hans-Joachim Vahlensieck, Wehr, both of Fed. Rep. of Germany

[73] Assignee: Dynamit Nobel AG, Cologne, Fed. Rep. of Germany

[21] Appl. No.: 446,756

[22] Filed: Dec. 3, 1982

[30] Foreign Application Priority Data

Dec. 28, 1981 [DE] Fed. Rep. of Germany ....... 3151677

[51] Int. Cl.$^3$ ............................ C07F 7/08; C07F 7/12
[52] U.S. Cl. .................................................. 556/467
[58] Field of Search ......................................... 556/467

[56] References Cited

U.S. PATENT DOCUMENTS 2,500,761  3/1950  Leuis ................................. 556/467
2,615,034 10/1952  Hyde ................................. 556/467
2,897,220  7/1959  Jenkner ........................ 556/467 X

FOREIGN PATENT DOCUMENTS 1111183  7/1961  Fed. Rep. of Germany ...... 556/467
1217954  6/1966  Fed. Rep. of Germany ...... 556/467

Primary Examiner—Paul F. Shaver
Attorney, Agent, or Firm—Felfe & Lynch

[57] ABSTRACT

The present invention relates to the cleavage of organosiloxanes with hydrogen chloride with the formation of organochlorosilanes. In accordance with the invention, this cleavage is performed at temperatures below 20° C., and the dihydrates and trihydrates of the hydrogen chloride are formed. These settle as the specifically heavier, liquid phase and thus can easily be separated from the organochlorosilanes. The preferred temperature range in which the procedure of the invention is performed is between +10° C. and −10° C., while yields of as much as 99% of the desired organochlorosilane are obtained. The process can also be performed continuously.

The inventive process is particularly useful because it can be used to convert contaminated organosiloxanes, such as used heat exchange or hydraulic oil materials, into useful products.

10 Claims, No Drawings

METHOD OF CLEAVING ORGANOSILOXANES

BACKGROUND OF THE INVENTION

The subject matter of the present invention is a method for the cleavage of organosiloxanes by means of hydrogen chloride, resulting in the formation of organochlorosilanes, which are important starting products for the preparation of protective-group reagents used, for example, in the production of synthetic penicillins. Furthermore, the organochlorosilanes are foreproducts for the broad fields of application of the organosilicon esters and silicones.

Organosiloxanes are often produced in contaminated form in many fields of activity. For example, hexamethyldisiloxane forms as a waste product in protective-group chemistry, or it is contained in addition to other siloxanes in used silicone oils which have served, for example, as heat carriers or hydraulic oils. There has formerly been virtually no use for these used silicone oils, so that they have had to be rendered harmless or destroyed in large quantities.

Several attempts have already been made to render the valuable organosiloxane wastes reusable by cleaving the siloxanes to chlorosilanes. On the other hand, the methylchlorosilanes, for example, have been available on a large technical scale only through Rochow synthesis, and therefore their supply is dependent upon this method of synthesis. Thionyl chloride, aluminum chloride and phosphorus trichloride have already been described as cleavage reagents. A disadvantage in the use of these compounds is the high percentage of byproducts which are produced, and whose separation entails additional expense.

It is furthermore also known to cleave siloxanes by means of hydrogen chloride. These attempts, however, were performed in the presence of water-binding additives, such as concentrated sulfuric acid or $ZnCl_2$ in order to influence the otherwise incomplete reaction. Here, again, undesired byproducts are formed.

In German Offenlegungsschrift No. 3,013,920 a method is described for performing the cleavage with hydrogen chloride at an excess hydrogen chloride pressure in order to arrive at a complete transformation to chlorosilanes, which otherwise cannot be achieved at room temperature. According to the procedure therein described, a high yield of the desired chlorosilanes is achieved, but this process has the disadvantage of the high technical complexity that is involved in working with hydrogen chloride under pressure.

The problem therefore existed of performing the cleavage of organichlorosilanes with hydrogen chloride such that the desired organochlorosilane will be produced directly in high yields by this reaction, and the investment in apparatus will be as low as possible.

THE INVENTION

As the solution to this problem, a method has been discovered for the cleavage of liquid monofunctional and bifunctional organosiloxanes of the formula $(R_3Si)_2O$ or those having $-R_2SiO-_x$ units, R representing identical or different alkyl or alkenyl moieties of 1 to 18 carbon atoms, substituted with halogen or aryl if desired, or representing aryl moieties, and x represents any desired degree of polymerization, in which method the organosiloxanes are reacted with hydrogen chloride with the formation of organochlorosilanes, this method being characterized by the fact that the hydrogen chloride is reacted with the organosiloxane at temperatures below 20° C., without the additional application of pressure, the hydrogen chloride hydrates forming in the reaction being allowed to settle as a liquid phase, and this liquid phase, saturated with hydrogen chloride, being removed from the system.

The reaction is generally performed by saturating the organosiloxane with the hydrogen chloride at the chosen reaction temperature, which is to be less than 20° C. During the reaction, the hydrogen chloride hydrates, known in themselves, develop, and settle as the heavy phase. Any stirring of the system is, of course, to be avoided.

The liquid phase which develops in the process of the invention consists mostly of mixtures of the dihydrate and trihydrate of the hydrogen chloride. The hydrate content depends on the saturation temperature; at 0° C., these two hydrates are present in an approximately equal ratio by weight.

In the organic, lighter phase are to be found the desired organochlorosilanes, which form in accordance with the following reactions:

$$3(R_3Si)_2O + 7HCl \rightarrow 6R_3SiCl + HCl.3H_2O \quad (1)$$

and

$$2-R_2SiO-_x + 5xHCl \rightarrow 2xR_2SiCl_2 + XHCL.2H_2O \quad (2)$$

In these equations, however, allowance must be made for the temperature dependence on the formation of the hydrogen chloride hydrate: at −20° C., it is mainly the dihydrate that is separated; the percentage of trihydrate is low at −20° C. At 0° C., the two hydrates are present in approximately equal proportion, while at 20° C. the trihydrate content greatly predominates and the dihydrate content is low.

The reaction of the invention can be performed at any temperature below 20° C., as long as the heavier phase is in the liquid aggregate state at this temperature; this means that it is possible to operate down to temperatures at which the freezing point of the hydrogen chloride hydrates is reached, which can be lowered, if desired, by the presence of mixtures causing a depression of the freezing point. Accordingly, it is possible in some cases to operate at temperatures as low as −25° C. However, the temperature range between +0° C. and −10° C. is especially preferred. Furthermore, within this range, if it is desired that the production of dialkyldichlorosilanes is to predominate, the most preferred temperature range is between 0° C. and −10° C., and in some cases even slightly lower, while if essentially only trialkylchlorosilanes are to be produced by the cleavage process of the invention, it is preferable to operate in the temperature range between 0° C. and +10° C.

The reaction in accordance with the invention can be performed either discontinuously or continuously. In either case it is desirable to first introduce the hydrogen chloride into the organosiloxane at the desired reaction temperature. A second liquid phase will result while the hydrogen chloride is being introduced as the cleavage reaction progresses; this second phase falls to the bottom as a result of its high specific weight, and can be removed either continuously or discontinuously at brief intervals of time. The introduction of the hydrogen chloride into the organosiloxane is continued until no more hydrogen chloride is absorbed by the organosiloxane. This can be detected by the release of hydrogen chloride (gas) from the reaction mixture and the cessation of formation and separation of the heavier (lower) liquid phase.

When a discontinuous procedure is followed, the hydrogen chloride feed is slowed as the reaction nears the endpoint and finally stopped so that the lower phase can be completely removed. This allows easier determination of the endpoint of the reaction when small amounts of hydrogen chloride are then introduced into the reaction. At this point, the upper phase consists of more than 99% of the desired chlorosilane.

When a continuous procedure is followed, an overflow tube for the desired organochlorosilane is advantageously provided in the upper part of the apparatus above the level of the charge of organosiloxane and the reaction commenced by introduction of hydrogen chloride. As soon as the organochlorosilane begins to overflow through tube, the feeding of additional organosiloxane is begun, preferably delivered to the lower part of the reactor. The amount of organosiloxane fed into the reactor is controlled to correspond to the overflow of the organochlorosilane and the amount of hydrogen chloride, of course, is matched to the amount of organosiloxanes being introduced, in accordance with the equations given above.

The organosiloxanes that can be used as starting products either contain structural units of the general formula $[R_2SiO]_x$ or they correspond to the general formula $(R_3Si)_2O$. In these formulas, R represents identical or different aryl, preferably phenyl, $C_1$–$C_{18}$ alkenyl, $C_1$–$C_{18}$ alkyl; $C_1$ to $C_{18}$ alkyl or alkenyl substituted by halogen preferably fluorine, chlorine or bromine, or aryl, preferably phenyl. The index x is an expression of the degree of polymerization in polysiloxanes, which can vary widely, as it is known (for example from 2 to about 2000); the index x can also assume a fractional value if, for example, a mixture of different bifunctional polysiloxanes of different degrees of polymerization is used.

The following are examples of cleavable organosiloxanes: All hexaalkyldisiloxanes, such as hexamethyldisiloxane and hexaethyldisiloxane, and the dimethylpolysiloxanes and the linear silicones as well as the linear content of branched or cyclic siloxanes and silicones, even when they contain, for example, vinyl, phenyl, trifluoropropyl, chloropropyl, chloromethyl, phenylethyl or even ethyl to octadecyl groups.

The siloxane compounds do not need to be used in pure form. The process of the invention can tolerate, in view of the reactivity of the hydrogen chloride, relatively large concentrations of contaminants, such as, for example, contents of chlorinated hydrocarbon substances or hydrocarbon substances in the siloxanes. This fact makes possible the very sought-after recovery of siloxane wastes which, in the inventive process, is relatively uncomplicated and inexpensive.

EXAMPLES

EXAMPLE 1

A vertically disposed double-jacketed tube of 50 mm inside diameter and 800 mm height, with a capacity of about 1.5 liters, equipped with a likewise double-jacketed drain cock, breather tube, internal thermometer and a gas introduction tube at the bottom end, was filled with 900 g of no longer serviceable polydimethylsilicone oil. This oil had formerly served as a heat carrier liquid at a temperature of about 200° C. and was contaminated with about 6% of kerosene.

The system was chilled to $-10°$ C. and then fed for 3 hours with 320 g/h of gaseous hydrogen chloride, while maintaining the reaction temperature at $-10°$ C., and the specifically heavier liquid phases that formed were let out through the draincock at intervals of about 20 minutes.

At the end of the three hours the rate of hydrogen chloride input was throttled to 130 g/h, and the reaction was allowed to continue at this rate under otherwise the same conditions until the hydrogen chloride was no longer being absorbed due to saturation, but began to flow out through the breather tube. This was the case after about another 30 minutes, whereupon the hydrogen chloride feed was cut off. The content of the reactor had expanded during the reaction to approximately 1.5 liters.

The mixture was allowed to stand for about 1 hour at 0° C., and then the last drops of the bottom phase were separated and the upper phase was distilled at standard pressure through a short column. At the boiling point of 70° C., a total of 1412 g of pure dimethyldichlorosilane distilled out after a few grams of first runnings (approximately 95% with respect to the polydimethylsiloxane input of approximately 840 g).

The specifically heavier phase totaling 388 g which separated during the reaction contained 47.3% of HCl and accordingly it consisted of about 70% of $HCl.2H_2O$ and only about 30% of $HCl.3H_2O$. A total of about 1050 g of gaseous hydrogen chloride had been used.

EXAMPLE 2

In a manner similar to Example 1, the reactor described therein was charged with 1156 g (5 moles) of 1,2-dichloromethyltetramethyldisiloxane and saturated for 2 hours with 190 g/h of hydrogen chloride, and then for 30 minutes with 100 g/h of hydrogen chloride, while a total of about 160 g of the bottom phase was separated at intervals of about 20 minutes (HCl concentration 43.2% corresponding to 32% of $HCl.2H_2O$ and 68% of $HCl.3H_2O$). The fill level in the reactor in the meantime rose from about 70% to about 90% of capacity due to the volume expansion taking place during the reaction. The gas chromatography of the upper phase showed approximately 98% of chloromethyldimethylchlorosilane. A total of 1389 g of this product was isolated by distillation.

EXAMPLE 3

A vertically disposed cylindrical, double-jacketed reactor of 80 mm diameter and 1000 mm height, having a capacity of about 5 liters and equipped with an internal thermometer, was provided at the top end with a breather tube and an overflow tube; at the bottom end it had a controlled-temperature drain cock and behind it a metering valve controlling the drainage of the bottom phase by means of a capacitive sensor. A tube for the introduction of hydrogen chloride and a tube for feeding siloxane opened into the reactor at approximately 200 mm above the bottom.

The reactor was charged with 3.4 kg of hexamethyldisiloxane, adjusted to an internal temperature of 0° C., and started up by feeding in 620 g/h of hydrogen chloride while removing 230 g of the bottom phase per hour. After about 3 hours, with the reactor completely filled and a maintained reaction temperature of 0° C., and with hydrogen chloride being introduced at the same rate, continuous operation was started by the delivery of 1140 g of hexamethyldisiloxane per hour. The hourly rate of removal of 230 g of bottom phase was continued. From then on, approximately 1500 g of the upper phase emerged per hour from the breather tube and overflow tube.

The upper phase consisted of an average of 96 to 98% of trimethylchlorosilane and a small amount of hexamethyldisiloxane. The bottom phase consisted of a mixture of about equal parts of hydrogen chloride dihydrate and trihydrate, with an average HCl content of 45.2%.

Over an operating period of 82 hours a total of 93.1 kg of hexamethyldisiloxane and 50.8 kg of hydrogen chloride were processed, and from them 120.5 kg of trimethylchlorosilane was produced (96.8% yield); 2.8 kg of hexamethyldisiloxane was recovered. 18.8 kg of 45.2% hydrogen chloroide hydrates was produced as byproduct.

EXAMPLE 4

As in Example 1, 821 g (2 mol) of a diffusion pump oil consisting mostly of 1,1,3,3-tetraphenyl-1,3-dimethyldisiloxane was saturated with hydrogen chloride at $-10°$ C. within one hour, approximately 170 g of hydrogen chloride being required for this purpose. In the meantime, approximately 70 g of bottom phase was separated in several portions (HCl content approx. 47%). The subsequent distillation of the upper phase produced, at a boiling point of 128° to 131° C. (1 mbar), 902 g of methyldiphenylchlorosilane, corresponding to a product yield of about 97%.

It will be understood that the specification and examples are illustrative but not limitative of the present invention and that other embodiments within the spirit and scope of the invention will suggest themselves to those skilled in the art.

What is claimed is:

1. A method of cleaving a liquid mono- and bifunctional organosiloxane of the formula $(R_3Si)_2O$ or having $[R_2SiO]_x$ units wherein each R represents an identical or different aryl, alkyl, alkenyl, halogen or aryl substituted alkyl, or halogen or aryl substituted alkenyl; and x is the degree of polymerization; by using hydrogen chloride as the cleaving agent and with the formation of organochlorosilanes;

comprising the steps of reacting the hydrogen chloride with the organosilane at temperatures below 20° C. and at atmospheric pressure;

allowing the hydrogen chloride hydrates formed by the reaction to settle as a bottom liquid phase; and removing the bottom liquid phase from the system.

2. The method of claim 1 wherein the reaction temperature is maintained above about $-25°$ C.

3. The method of claim 1 wherein the reaction temperature is between about $-10°$ C. and $+10°$ C.

4. The method of claim 3 wherein the reaction temperature is above about 0° C.

5. The method of claim 3 wherein the reaction temperature is below about 0° C.

6. The method of claim 3 wherein hydrogen chloride is introduced into the reaction mixture until a saturated solution is obtained.

7. The method of claim 1 wherein the reaction temperature is above about 0° C.

8. The method of claim 1 wherein the reaction temperature is below about 0° C.

9. The method of claim 1 wherein the bottom liquid phase is continuously removed and, at the same time, corresponding amounts of hydrogen chloride and organosiloxane are continuously added to the system.

10. The method of claim 1 wherein the organosiloxane is polydimethylsilicone oil contaminated with kerosene.

* * * * *